US00PP24377P2

(12) United States Plant Patent
Beekenkamp

(10) Patent No.: US PP24,377 P2
(45) Date of Patent: Apr. 8, 2014

(54) ***BEGONIA* PLANT NAMED 'BKPBEEGW'**

(50) Latin Name: *Begona hiemalis*
Varietal Denomination: BKPBEEGW

(75) Inventor: Annie Cornelia Beekenkamp, Maasdijk (NL)

(73) Assignee: Beekenkamp Plants B.V., Maasdijk (NL)

( * ) Notice: Subject to any disclaimer, the term of this patent is extended or adjusted under 35 U.S.C. 154(b) by 26 days.

(21) Appl. No.: 13/507,636

(22) Filed: Jul. 13, 2012

(51) Int. Cl.
*A01H 5/00* (2006.01)

(52) U.S. Cl.
USPC ..... Plt./345

(58) Field of Classification Search
USPC ..... Plt./345
See application file for complete search history.

*Primary Examiner* — Kent L Bell
(74) *Attorney, Agent, or Firm* — C. A. Whealy

(57) ABSTRACT

A new and distinct cultivar of *Begonia* plant named 'BKPBEEGW', characterized by its broadly upright, somewhat outwardly spreading and mounded plant habit; moderately freely basal branching habit; medium-size leaves; uniform and freely flowering habit; and double flowers that are white in color on both the upper and lower surfaces.

2 Drawing Sheets

Botanical designation: *Begonia hiemalis*.
Cultivar denomination: 'BKPBEEGW'.

BACKGROUND OF THE INVENTION

The present invention relates to a new and distinct cultivar of *Begonia* plant, botanically known as *Begonia hiemalis*, commercially referred to as a Elatior *Begonia* and hereinafter referred to by the name 'BKPBEEGW'.

The new *Begonia* plant is a product of a planned breeding program conducted by the Inventor in Amstelveen, The Netherlands. The objective of the breeding program was to develop new freely branching and freely flowering *Begonia* plants with attractive foliage and flower colors.

The new *Begonia* plant is a naturally-occurring branch mutation of *Begonia hiemalis* 'BKPBEEGL', disclosed in U.S. Plant Pat. No. 23,825. The new *Begonia* plant was discovered and selected by the Inventor on a single flowering plant within a population of plants of 'BKPBEEGL' in a controlled greenhouse environment in Amstelveen, The Netherlands in October, 2010.

Asexual reproduction of the new *Begonia* plant by tip cuttings in a controlled greenhouse environment in Amstelveen, The Netherlands since February, 2011 has shown that the unique features of this new *Begonia* plant are stable and reproduced true to type in successive generations.

SUMMARY OF THE INVENTION

Plants of the new *Begonia* have not been observed under all possible environmental conditions and cultural practices. The phenotype may vary somewhat with variations in environmental conditions such as temperature and light intensity, without, however, any variance in genotype.

The following traits have been repeatedly observed and are determined to be the unique characteristics of 'BKPBEEGW'. These characteristics in combination distinguish 'BKPBEEGW' as a new and distinct *Begonia* plant:

1. Broadly upright, somewhat outwardly spreading and mounded plant habit.

2. Moderately freely basal branching habit.
3. Medium-size leaves.
4. Uniform and freely flowering habit.
5. Double flowers that are white in color on both the upper and lower surfaces.

Plants of the new *Begonia* can be compared to plants of the parent, 'BKPBEEGL'. Plants of the new *Begonia* differ from plants of 'BKPBEEGL' primarily in flower color as plants of 'BKPBEEGL' have pink-colored flowers. In addition, plants of the new *Begonia* are not as compact as plants of 'BKPBEEGL'.

Plants of the new *Begonia* can be compared to plants of the *Begonia* 'Bonbon White', not patented. In side-by-side comparisons conducted in Amstelveen, The Netherlands, plants of the new *Begonia* differed from plants of 'Bonbon White' in the following characteristics:

1. Plants of the new *Begonia* were more compact than plants of 'Bonbon White'.
2. Plants of the new *Begonia* and 'Bonbon White' differed slightly in flower color.

BRIEF DESCRIPTION OF THE PHOTOGRAPHS

The accompanying colored photographs illustrate the overall appearance of the new *Begonia* plant showing the colors as true as it is reasonably possible to obtain in colored reproductions of this type. Colors in the photographs may differ slightly from the color values cited in the detailed botanical description which accurately describe the colors of the new *Begonia* plant.

The photograph on the first sheet comprises a side perspective view of a typical flowering plant of 'BKPBEEGW' grown in a container.

The photograph on the second sheet is a close up view of the upper and lower surfaces of typical flower buds, flowers and leaves of 'BKPBEEGW'.

DETAILED BOTANICAL DESCRIPTION

Plants used for the aforementioned photographs and following observations and measurements were grown in 11-cm containers during the spring in a glass-covered greenhouse in Maasdijk, The Netherlands. During the production of the plants, day temperatures ranged from 19° C. to 20° C., night temperatures ranged from 18° C. to 19° C. and light levels averaged 6,000 lux. Plants were eleven weeks old when the photographs and the description were taken. In the following description, color references are made to The Royal Horticultural Society Colour Chart, 2007 Edition, except where general terms of ordinary dictionary significance are used.

Botanical classification: *Begonia hiemalis* 'BKPBEEGW'.

Parentage: Naturally-occurring branch mutation of *Begonia hiemalis* 'BKPBEEGW', disclosed in U.S. Plant Pat. No. 23,825.

Propagation:

*Type*.—By tip cuttings.

*Time to initiate roots, summer and winter*.—About 20 days at temperatures of about 25° C.

*Time to produce a rooted young plant, summer and winter*.—About 35 to 36 days at temperatures of about 21° C. to 23° C.

*Root description*.—Medium in thickness, fibrous; white in color; plants of the new *Begonia* have not been observed to form tubers.

*Rooting habit*.—Moderate branching; medium density.

Plant description:

*Plant form and growth habit*.—Broadly upright, somewhat outwardly spreading and mounded plant habit; plant shape roughly globular; moderately freely basal branching with about seven basal branches per plant; moderately vigorous growth habit.

*Plant height*.—About 21.8 cm.

*Plant width*.—About 29.7 cm.

*Branch description*.—Length: About 12.3 cm. Diameter: About 8 mm. Internode length: About 3.1 cm. Texture: Moderately to densely pubescent. Aspect: Upright to about 30° from vertical. Color, developing: Close to 173A. Color, fully developed: Between 148A and 152A.

*Leaf description*.—Arrangement: Alternate, simple. Length: About 12.1 cm. Width: About 8.1 cm. Shape: Ovate. Apex: Bluntly acute. Base: Oblique to hastate and imbricate. Margin: Bi-serrate to bi-crenate. Texture, upper surface: Smooth, glabrous; velvety. Texture, lower surface: Sparsely pubescent. Venation pattern: Palmate; reticulate. Color: Developing leaves, upper surface: Close to 147A; margins, tinged with close to 175A. Developing leaves, lower surface: Close to 183D. Fully expanded leaves, upper surface: Darker than between 147A and N189A; venation, close to 143A. Fully expanded leaves, lower surface: Close to 185C tinged with close to 148B; venation, close to 148A. Petioles: Length: About 4.7 cm. Diameter: About 5 mm. Texture, upper and lower surfaces: Moderately pubescent. Color, upper surface: Close to 185A; distally slightly tinged with close to 183A. Color, lower surface: Close to 174A; distally strongly tinged with close to 185A.

Flower description:

*Flowering habit*.—Double rotate sterile flowers arranged in axillary compound cymes; freely flowering habit with about eight flowers per cyme and about 280 flowers developing per plant; flowers face upright to outwardly.

*Fragrance*.—None detected.

*Natural flowering season*.—Plants begin flowering about 65 days after planting; long flowering period, plants flower freely and continuously from spring until autumn in The Netherlands.

*Flower longevity*.—Individual flowers last about ten days on the plant; flowers not persistent.

*Inflorescence height*.—About 14.8 cm.

*Inflorescence diameter*.—About 9.8 cm.

*Flower diameter*.—About 5.7 cm.

*Flower height*.—About 2.2 cm.

*Flower buds*.—Length: About 1.8 cm. Diameter, flattened: About 1.5 cm. Shape, flattened: Orbicular. Color: Close to 145D; towards the base, close to 145B.

*Tepals*.—Quantity per flower and arrangement: Four in a single whorl; two upper and two lower tepals. Upper tepals: Length: About 2.9 cm. Width: About 2.4 cm. Shape: Obovate. Apex: Rounded. Margin: Crenate; undulate. Texture, upper and lower surfaces: Smooth, glabrous; slightly velvety. Color: When opening, upper surface: Close to NN155C to NN155D; towards the base, close to 157A to 157B. When opening, lower surface: Close to NN155C to NN155D; towards the base, close to 157C. Fully opened, upper surface: Close to NN155D; towards the base, close to 155D; color does not change with development. Fully opened, lower surface: Close to NN155D; towards the base, close to 155A; color does not change with development. Lower tepals: Length: About 3.2 cm. Width: About 3.2 cm. Shape: Broadly obovate to orbicular. Apex: Rounded. Margin: Entire; undulate. Texture, upper and lower surfaces: Smooth, glabrous; slightly velvety. Color: When opening, upper and lower surfaces: Close to 150D; towards the base, close to 150C. Fully opened, upper and lower surfaces: Close to NN155C; center, close to NN155A; towards the base, close to 150D; color does not change with development.

*Tepaloids*.—Quantity and arrangement: About 20 arranged in several whorls. Length: About 1.6 cm. Width: About 1.1 cm. Shape: Obovate. Apex: Rounded. Margin: Crenate; undulate. Texture, upper and lower surfaces: Smooth, glabrous; slightly velvety. Color: When opening, upper and lower surfaces: Close to NN155B; towards the base, close to 150C. Fully opened, upper surface: Close to NN155C; towards the base, close to 154C; color does not change with development. Fully opened, lower surface: Close to NN155C; towards the base, close to 150D; color does not change with development.

*Flower bracts*.—Quantity per flower: One. Length: About 1.4 cm. Diameter: About 1.5 cm. Color: Close to 145A to 145B; margins, close to 182A.

*Peduncles*.—Length: About 7.2 cm. Diameter: About 3.5 mm to 4 mm. Angle: About 30° from branch axis. Texture: Smooth, glabrous. Color: Close to 152B.

*Pedicels*.—Length: About 1.8 cm. Diameter: About 2 mm. Angle: About 40° from the peduncle axis. Texture: Densely pubescent. Color: Close to 145B.

*Reproductive organs*.—Reproductive organ development has not been observed on flowers of plants of the new *Begonia*.

*Seeds and fruits*.—Seed and fruit development production has not been observed on plants of the new *Begonia*.

Disease & pest resistance: Resistance to pathogens and pests common to *Begonia* has not been observed on plants of the new *Begonia*.

Temperature tolerance: Plants of the new *Begonia* have been observed to tolerate temperatures from about 14° C. to about 35° C.

It is claimed:

1. A new and distinct *Begonia* plant named 'BKPBEEGW' as illustrated and described.

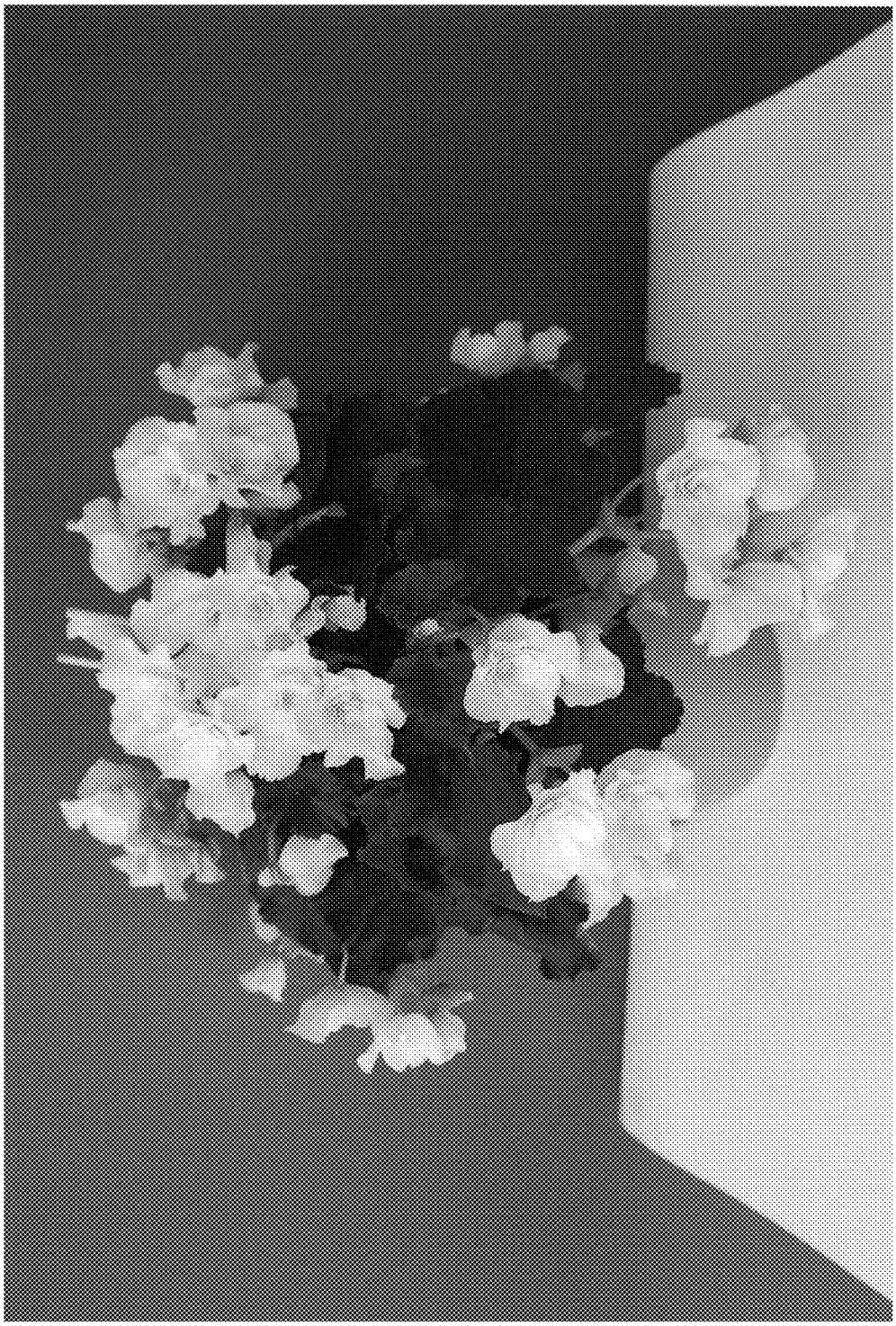

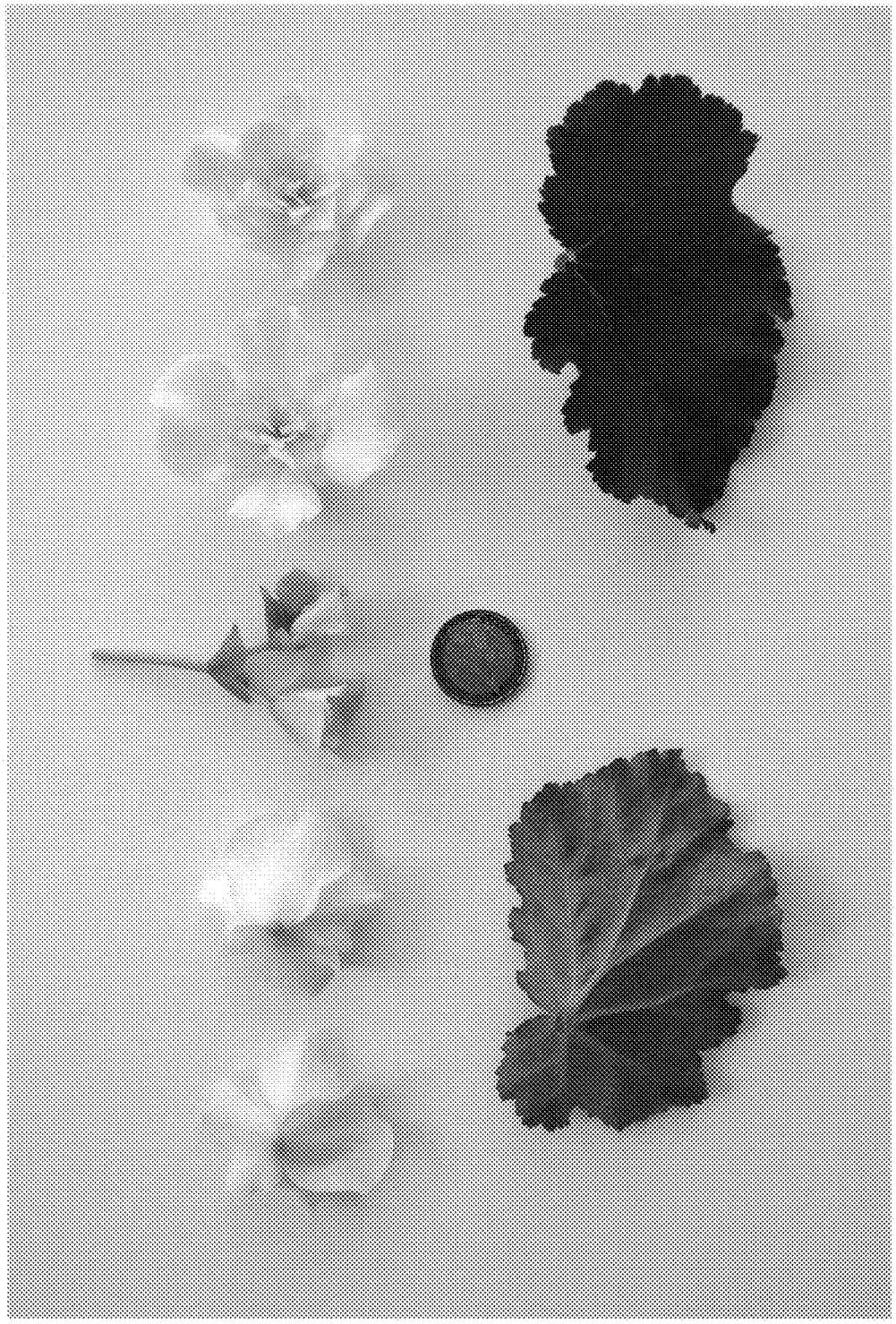

* * * * *